(12) United States Patent
Kim (10) Patent No.: US 8,093,051 B2
(45) Date of Patent: Jan. 10, 2012

(54) METHOD FOR ISOLATION OF INNER CELL MASS AND METHOD OF PREPARATION OF EMBRYONIC STEM CELL LINES USING INNER CELL MASS ISOLATED BY THE SAME

(76) Inventor: Chang Hyun Kim, Las Vegas, NV (US)

( * ) Notice: Subject to any disclaimer, the term of this patent is extended or adjusted under 35 U.S.C. 154(b) by 357 days.

(21) Appl. No.: 12/459,869

(22) Filed: Jul. 10, 2009

(65) Prior Publication Data

US 2010/0248367 A1    Sep. 30, 2010

(30) Foreign Application Priority Data

Mar. 29, 2009  (KR) .................. 10-2009-0026713
May 25, 2009   (KR) .................. 10-2009-0045648

(51) Int. Cl.
*C12N 5/00*   (2006.01)

(52) U.S. Cl. ......... 435/378; 435/325; 435/347; 435/379

(58) Field of Classification Search .................. None
See application file for complete search history.

(56) References Cited

OTHER PUBLICATIONS

Skottman et al. Reprod 2006;132:691-8.*
Shi et al. Dev Dynamics 2008;237-640-8.*
Nick Strelchenkoi, Oleg Verlinsky, Valeri Kukharenko, and Yury Verlinsky, Morula-derived human embryonic stem cells, Reproductive BioMedicine, vol. 9, No. 6, 2004, 623-629, Oct. 27, 2004.
Tenneille E Ludwig, Veit Bergendahl, Mark E Levenstein, Junying Yu, Mitchell D Probasco & James A Thomson, Feeder-independent culture of human embryonic stem cells, Nature Methods, vol. 3, No. 8, 637-646, Aug. 2006 (Published online Jul. 2006).
Svetlana Gavrilov, Robert W Prosser, Imran Khalid, Joanne MacDonald, Mark V Sauer, Donald W Landry, & Virginia E Papaioannou, Non-viable human embryos as a source of viable cells for embryonic stem cell derivation, Reproductive BioMedicine, vol. 18, No. 2, 2009, 301-308, Dec. 9, 2008.
Nick Strelchenko and Yury Verlinsky, Embryonic Stem Cells from Morula, Methods in Enzymology, vol. 418: Embryonic Stem Cells, 93-108, Academic Press, 2006.

* cited by examiner

*Primary Examiner* — Q. Janice Li
(74) *Attorney, Agent, or Firm* — The PL Law Group, PLLC (57) ABSTRACT

A method for isolation of an inner cell mass and a method for preparation of embryonic stem cell lines using the inner cell mass isolated by the same. A blastocyst being free from a zona pellucida removed therefrom is placed on a feeder cell, and a micro cover glass is put on the blastocyst to apply pressure caused by a weight of the micro cover glass, to the blastocyst for a desired time, so that the inner cell mass may be obtained with considerably improved yield compared to conventional methods, and therefore, an embryonic stem cell line may be efficiently established and proliferated.

18 Claims, 9 Drawing Sheets

METHOD FOR ISOLATION OF INNER CELL MASS AND METHOD OF PREPARATION OF EMBRYONIC STEM CELL LINES USING INNER CELL MASS ISOLATED BY THE SAME

CLAIM OF PRIORITY

This application claims priorities to Korean Patent Applications No. 2009-26713 filed on Mar. 29, 2009 and 2009-45648 filed on May 25, 2009 in the Korean Intellectual Property Office, the entire contents of which are hereby incorporated by reference.

BACKGROUND OF THE INVENTION

1. Field of the Invention

The present invention relates to a method for isolation and cultivation of an inner cell mass, and a method for preparation of embryonic stem cell lines using the inner cell mass isolated by the same.

2. Description of the Related Art

A sperm is combined with an ovum to form a single fertilized ovum and the fertilized ovum begins cell division and forms a solid sphere of cells called a blastocyst. The blastocyst possesses an inner cell mass (ICM), which comprises plural cells to form an embryo through cell division and cell differentiation. The embryo develops into a fetus, then, an individual after a gestational period.

When cells of the inner cell mass are isolated from the blastocyst and cultured under desired conditions, a cell having potential for differentiation may be obtained although no more differentiation proceeds in this cell. Such cell refers to an embryonic stem cell. Briefly, the embryonic stem cell is a cell derived from the inner cell mass of an early stage of embryo, and the embryonic stem cell remains undifferentiated but has potential to differentiate into any type of cell and/or tissue found in organs of an individual.

In other words, the embryonic stem cell is pluripotent. The embryonic stem cell may indefinitely repeat cell division in theory. Based on these characteristics, it is expected the embryonic stem cell may be effectively used for regeneration of a tissue after injury or disease. In particular, a number of researches and investigation into embryonic stem cell therapies have been increasingly conducted since Thomson et. al. (1998) succeeded in cultivation of human embryonic stem cells.

Accordingly, isolation of an inner cell mass as a precondition for formation of the embryonic stem cell has also been recently studied. Among such isolation methods, immunosurgery is well known and commonly used. The immunosurgery method will be described as follows.

First, a zona pellucida of a fertilized ovum is dissolved in 0.1% pronase for 1 to 2 minutes. Then, a blastocyst cell mass present in the zona pellucida is stored in a 100% anti-human serum antibody solution (Sigma) for about 20 minutes, followed by storing again the blastocyst cell mass in a guinea pig complement for about 30 minutes, so as to destroy a trophoblast layer and isolate the inner cell mass from the blastocyst. As described above, such immunosurgery method for isolation of an inner cell mass is based on chemical treatment.

The isolated inner cell mass by immunosurgery is fixed to a fetal fibroblast (that is, feeder cell) then proliferated and, when a density and a size of the proliferated cell mass are increased, it may be considered that formation of an embryonic stem cell line is completed. Such formed embryonic stem cell is separated into smaller cell colonies, which are in turn transferred to a fresh culture dish (such as Petri-dish) under the same culturing conditions in order to repeat subculturing thereof, so that the cell colonies are continuously proliferated while remaining undifferentiated. Repeating the above processes may produce a number of embryonic stem cells.

However, since the immunosurgery described above adopts immunological and/or chemical treatment to destroy a blastocyst in order to isolate an inner cell mass contained in the blastocyst, the isolated cells often fail to be fixed to the feeder cell. Further, such chemical treatment encounters a problem in that the isolated inner cell mass cannot remain un-differentiated, instead being differentiated into undesired cells, therefore, the desired un-differentiated embryonic stem cell line may not be efficiently established.

Accordingly, the immunosurgery method has a restriction in number of embryonic stem cell lines successfully established by culturing plural cells on a feeder cell, since the number of the embryonic stem cell lines generally ranges from 10 to 20% of a total number of fertilized ova used in the isolation.

SUMMARY OF THE INVENTION

According to an aspect of the present invention, a method for isolation and cultivation of an inner cell mass by mechanically handling a blastocyst instead of chemical treatment is provided.

Another aspect of the present invention is to provide a method for isolation and cultivation of an inner cell mass using a micro cover glass with a desired weight sufficient to apply pressure to a blastocyst, wherein the inner cell mass is efficiently isolated while remaining un-differentiated.

A still further aspect of the present invention is to provide a method for preparation of an embryonic stem cell line with improved yield by proliferating the inner cell mass isolated according to the above method, on a feeder cell.

According to an aspect of the present invention, there is provided a method for isolation of an inner cell mass including: placing a blastocyst being free from a zona pellucida on a feeder cell; putting a micro cover glass on the blastocyst to cover and apply pressure to the blastocyst for a desired time to destroy a trophoblast layer and isolate the inner cell mass from the blastocyst; and removing the micro cover glass from the isolated inner cell mass.

According to an embodiment of the present invention, the micro cover glass may have a lifting part.

According to an embodiment of the present invention, the lifting part may be a ring or a bent end of the micro cover glass.

According to an embodiment of the present invention, the pressure caused by the weight of the micro cover glass may range from 0.001 to 0.003 $g/mm^2$.

According to an embodiment of the present invention, a period of time to cover the blastocyst with the micro cover glass may range from 3 to 20 hours.

Preferably, the period of time to cover the blastocyst with the micro cover glass ranges from 13 to 15 hours.

According to an embodiment of the present invention, the micro cover glass may have a size of 3 to 8 mm in width and 2 to 6 mm in length.

According to an embodiment of the present invention, a tool selected from pincettes, forceps or a micro-manipulator may be used to cover the blastocyst with the micro cover glass or to remove the micro cover glass from the blastocyst after a desired period of time.

According to an embodiment of the present invention, the blastocyst having the zona pellucida removed therefrom may be treated using trichostatin-A beforehand.

According to another aspect of the present invention, there is provided a method for preparation of an embryonic stem cell line, comprising proliferating the inner cell mass isolated by the isolation method as defined in any one of the above-mentioned method for isolation of an inner cell mass on a feeder cell.

According to an aspect of the present invention, there is provided a method for isolation of an inner cell mass including: placing a blastocyst being free from a zona pellucida on a feeder cell; and putting a cover on the blastocyst with a space ranging from 4 micrometer to 40 micrometer between the cover and the feeder cell to destroy a trophoblast layer and isolate the inner cell mass from the blastocyst.

According to an embodiment of the present invention, a spacer is present on at least one of the cover and the feeder cell or between the cover and the feeder cell to make the space ranging from 4 micrometer to 40 micrometer between the cover and the feeder cell.

According to an embodiment of the present invention, the spacer is legs mounted on the cover, and the legs have a length of 4 micrometer to 40 micrometer to make the space between the cover and the feeder cell when the cover is put on the blastocyst.

According to an embodiment of the present invention, the spacer is a glass fiber put on the blastocyst, a nylon filament or a plastic filament.

According to an embodiment of the present invention, the space ranges from 10 micrometer to 30 micrometer.

According to an embodiment of the present invention, the space ranges from 20 micrometer to 30 micrometer.

The inner cell mass obtained according to the inventive method for isolation and cultivation shows remarkably high fixation rate to a feeder cell, thus being effectively used for preparation of an embryonic stem cell line. In addition, the present invention does not adopt chemical treatment of the blastocyst, thereby advantageously retaining the inner cell mass un-differentiated.

In particular, the isolation method of the present invention optimally derives natural alteration of the blastocyst by applying a desired pressure only to the blastocyst, so as to effectively prevent generation of a trophoblast layer as a wall layer to hold the inner cell mass during culturing. Hence, the inventive method may be useful for preparation of un-differentiated embryonic stem cell lines.

The embryonic stem cell prepared according to the present invention forms embryos under differentiation conditions and has greater potential to differentiate into various cell types and/or tissues. Moreover, the embryonic stem cell may continuously have cytological, immunological and/or genetic characteristics of un-differentiated cells under un-differentiation conditions.

A method for preparation of stem cell lines according to an embodiment of the present invention shows high success rate, which is substantially 4 times higher than that of conventional immunosurgery (not more than 20%).

In addition, the inventive isolation method is performed within a short processing time and adopts a simple procedure, compared to immunosurgery.

Accordingly, the method for isolation and cultivation of an inner cell mass and the method for preparation of an embryonic stem cell line according to the present invention may be suitably used in medical applications and/or studies using human embryonic stem cells.

BRIEF DESCRIPTION OF THE DRAWINGS

These and other objects, features, aspects, and advantages of the present invention will be more fully described in the following detailed description of preferred embodiments and examples, taken in conjunction with the accompanying drawings. In the drawings.

DETAILED DESCRIPTION OF THE INVENTION

Hereinafter, exemplary embodiments of the present invention will be described in greater detail with reference to the accompanying drawings.

An embodiment of the present invention describes a method for isolation and cultivation of an inner cell mass. A primordial embryo such as a morula and a blastocyst from which a zona pellucida has been removed (i.e., a morula or a blastocyst being free from a zona pellucida) is placed on a feeder cell or a medium for the feeder-independent maintenance and expansion of human embryonic stem cells (hESC) in the undifferential state, which is referred to as "feeder-independent medium" hereinafter. Examples of the feeder-independent medium include mTsSR™ or mTeSR™ medium (available from Stem Cell Technologies). A cover (e.g., micro cover glass) is put on the blastocyst to cover and apply pressure to the blastocyst for a certain period of time wherein the pressure is naturally caused by a weight of the micro cover glass, so that the inner cell mass may be obtained with considerably improved yield compared to a conventional method, and hence, an embryonic stem cell line may be efficiently established and proliferated.

According to an embodiment of the inventive method, a blastocyst obtained by fertilization and in vitro culture is used. The blastocyst generally comprises about 100 to 200 cells. More particularly, the blastocyst has a specified structure of viviparous mammals, characterized by 30 to 40 cells called an inner cell mass as well as a trophoblast layer as a wall layer enclosing the inner cell mass. According to multiple stages for differentiation of a fertilized ovum, it may also be possible to partially extract stem cells from the fertilized ovum with stopped growing, although it is invisible to the naked eye.

The zona pellucida of the blastocyst may be removed, for example, by dissolving it in 0.1% pronase for 1 to 2 minutes.

For a human blastocyst, pre-treating the zona pellucida-free blastocyst in, for example, 25 to 125 nmol/ml of trichostatin-A for about 4 hours may prevent genetic methylation thereof, thereby enhancing growth of a fertilized ovum. More particularly, when a single pronucleus is formed after artificial fertilization (by introducing sperms into a drop containing ovum), the pronucleus is first incubated in a culture solution containing 35 to 40 nmol/ml of trichostatin-A (TSA) for 4 hours, followed by transferring the cultured pronucleus to another culture solution without TSA then further culturing the same.

The feeder cell used in an embodiment of the present invention is a mouse fetal fibroblast having reduced differentiation potential by chemical treatment using mitomycin C or radiation treatment beforehand. The feeder cell does not show self-reproduction, while assisting inhibition of differentiation of an embryonic stem cell and assisting proliferation thereof.

Compared to a mouse embryonic stem cell, a human embryonic stem cell requires a feeder cell in order to proliferate while remaining undifferentiated. Cultivation of human embryonic stem cells has been performed using a mouse embryonic fibroblast (MEF) as a feeder cell layer. In recent years, studies and investigation into use of human derived cells in culturing, instead of cells of different species such as a mouse, have been increasingly conducted. Therefore, the feeder cell is not particularly limited to MEFs.

The micro cover glass used in an embodiment of the present invention may include a thin cover glass typically used in biotechnological applications and is not particularly restricted so long as the glass sufficiently covers a blastocyst and does not destroy the blastocyst when loading and/or unloading the glass. The micro cover glass may be loaded or unloaded using a tool such as pincettes, forceps, micro-manipulator, etc.

The micro cover glass used in an embodiment of the present invention may have a lifting part to more easily load or unload the micro cover glass. In this case, the micro cover glass consists of a cover part to cover the blastocyst and the lifting part coming in contact with the blastocyst when loading or unloading the same. If a pair of pincettes or forceps or the micro-manipulator is used to load or unload the micro cover glass, the lifting part may be a portion coming in contact with the above tool.

Figure 1A:
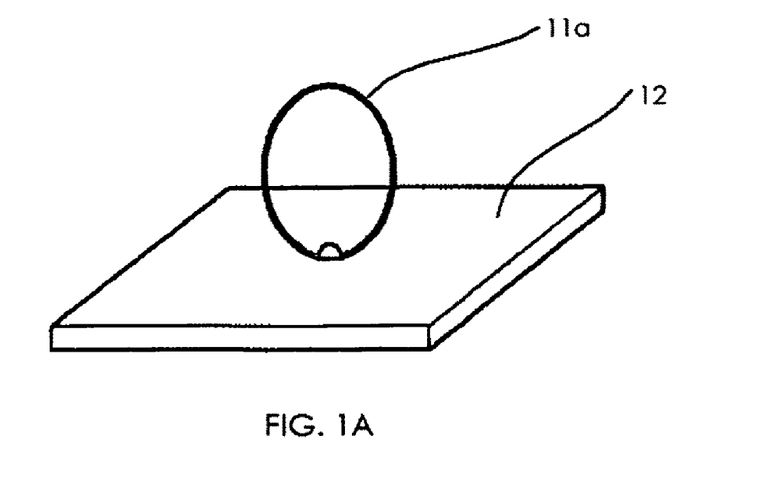
FIGS. 1A to 1C are views illustrating examples of a lifting part according to an exemplary embodiment of the present invention.
Figure 1B:
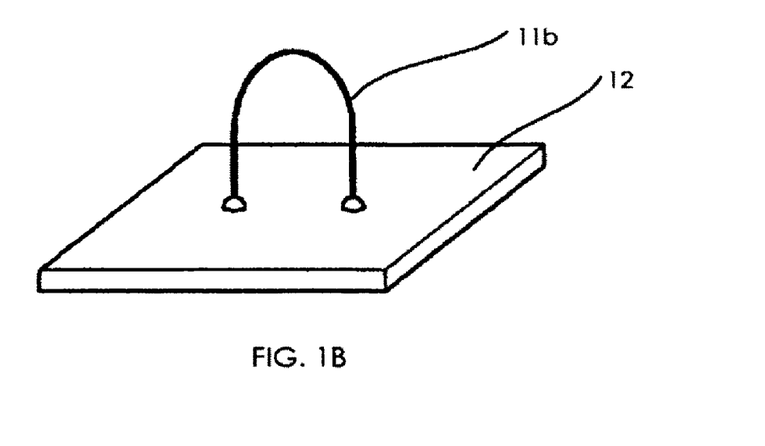
Figure 1C:
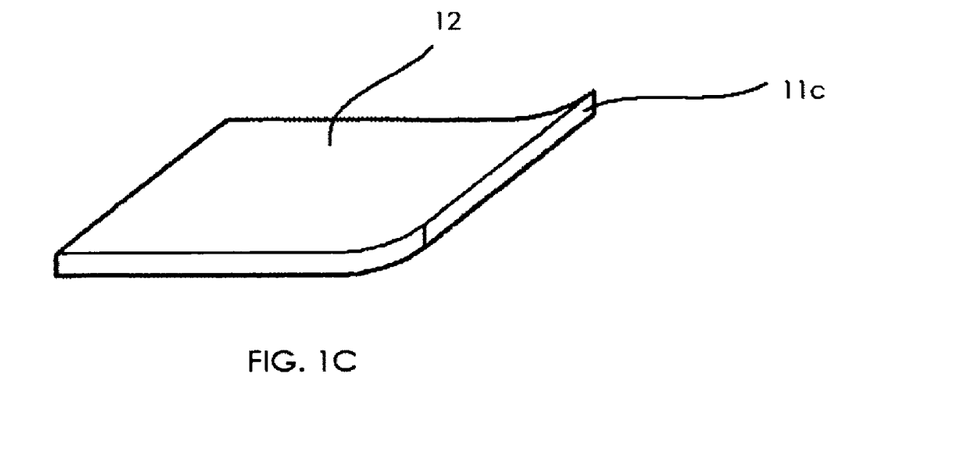

Examples of the lifting part are shown in FIGS. 1A to 1C. The lifting part may be a wire part 11a and 11b attached to the cover (e.g., micro cover glass 12) (see FIG. 1A and FIG. 1B). A fine wire may be mounted on a top of the micro cover glass in a ring form as shown in FIG. 1A. Methods of attaching the fine wire to the top of the micro cover glass are not particularly limited. For instance, after a glass is fused using a micro forge (MF-900 narishige) device, a fine wire is adhered to the fused glass.

The lifting part may also be a part 11c of the micro cover glass 12. For instance, when heating an end of the micro cover glass, the heated end part is bent due to a weight of the micro cover glass. If the bent part can be gripped using a tool such as pincettes or forceps, the end part of the micro cover glass may function as the lifting part (see FIG. 1c).

Figure 2A:
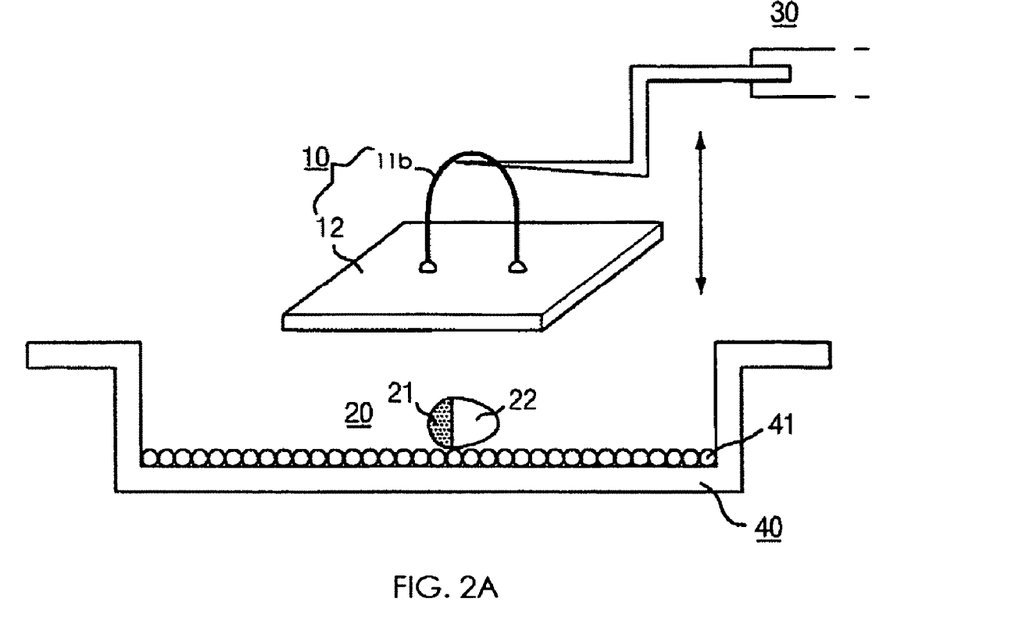
FIGS. 2A and 2B are views illustrating use of a micro cover glass having a lifting part.
Figure 2B:
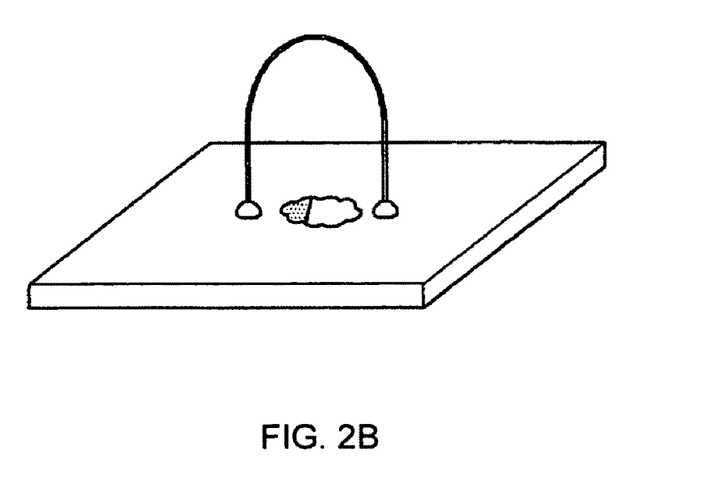

FIG. 2A shows use of a cover 10 comprised of a micro cover glass 12 having a lifting part 11b. A blastocyst is placed on a feeder cell 41 (FIG. 2A) on a culture dish 40 and, using a micro-manipulator 30, the micro cover glass gently covers the blastocyst 20 which in turn presses the blastocyst 20 comprised of a trophoblast layer 22 and an inner cell mass 21 owing to a weight of the micro cover glass 12 (FIG. 2B).

For preparation of a human embryonic stem cell line, the micro cover glass may have a size of 3 to 8 mm in width and 2 to 6 mm in length in consideration of size of the blastocyst. For the micro cover glass having a size of 5 mm×5 mm, the weight of the micro cover glass may range from 0.008 to 0.01 g and the blastocyst may receive a load of about 0.002 g per unit area (1 mm×1 mm) of the cover glass.

The micro cover glass may cover the blastocyst for about 3 to 20 hours. For a human blastocyst, the covering time preferably ranges from 13 to 15 hours. When covering the blastocyst with the micro cover glass or taking off the micro cover glass from the blastocyst after a certain time, the blastocyst should be carefully managed not to collapse or damage it. Considering this fact, a micro-manipulator is preferably used.

According to another embodiment of the present invention, a space may be provided between a cover covering the blastocyst and a feeder cell. The space may be 4 micrometer to 40 micrometer. When such a space between the cover and the feeder cell is present, the inner cell mass may be fixed to the feeder cell more efficiently, and the culture solution may flow freely so that a more efficient cell culture may be achieved.

The space can be provided in various ways. For example, a spacer may be positioned between a cover and a feeder cell or on a cover and/or a feeder cell.

Figure 3A:
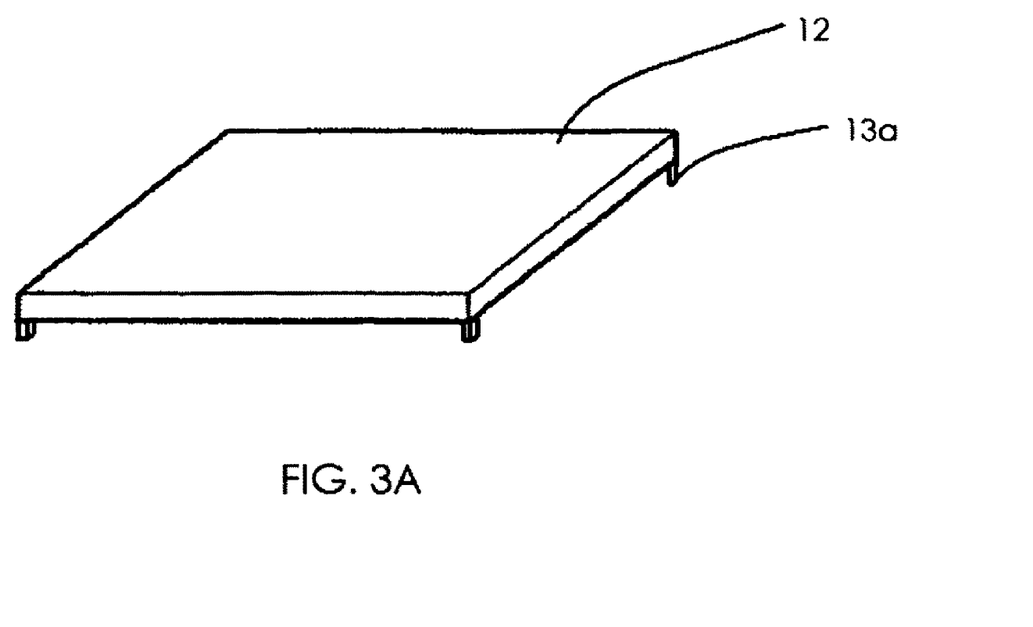
FIGS. 3A and 3B are views illustrating examples of a spacer according to an exemplary embodiment of the present invention.

One of the examples of the spacer on the cover is shown in FIG. 3A. In this example, the spacer is legs 13a mounted on the cover 12. The number and the shape of the legs are not particularly limited.

Figure 3B:
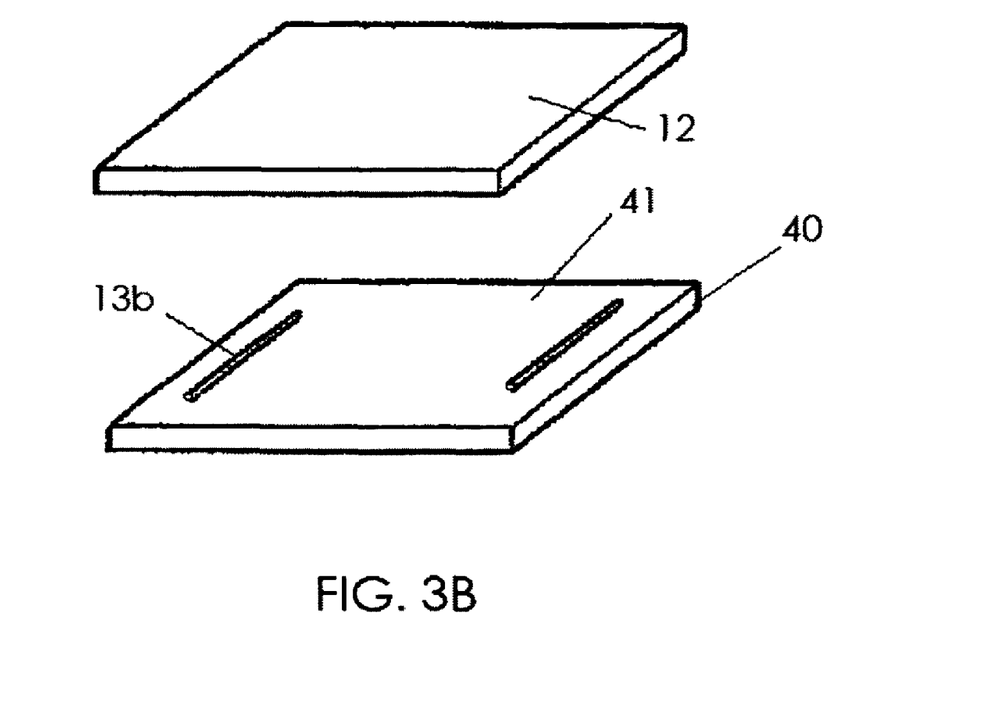

According to another example of the spacer, a glass fiber 13b may be a spacer. The glass fiber 13b is put on the feeder cell 41 in the culture dish 40.

When the cover is put on the blastocyst, the glass fiber 13b makes a space between the cover 12 and the feeder cell 41 on the culture dish 40. Alternatively, a filament such as a nylon filament or a plastic filament (e.g., dental floss) may be used as a spacer.

According to an embodiment of the present invention, the spacer may make a space of about 4 micrometer to 40 micrometer. According to another embodiment of the present invention, the spacer may make a space of about 10 micrometer to 30 micrometer. According to still another embodiment of the present invention, the spacer may make a space of about 20 micrometer to 30 micrometer.

An inner cell mass (ICM) isolated according to the inventive isolation method may proliferate on another feeder cell in order to form an embryonic stem cell line. Proliferation of the isolated ICM and preparation of the embryonic stem cell line using the proliferated ICM may be performed by any procedure well known in biological applications without particular limitation thereof. However, according to the isolation method of the present invention, the ICM is obtained in large quantities and exhibits a high fixation rate on the feeder cell and a high success rate of culturing ICM on the feeder cell. Hence, a possibility for establishment of the embryonic stem cell line may be noticeably increased even by any known process, compared to conventional methods.

A culture solution may include any solution commonly used in culturing embryonic stem cells. In particular, the culture solution is preferably prepared by adding 0.1 mM β-mercaptoethanol (Sigma), 100 units/ml penicillin, 100 μg/ml streptomycin and 4 ng/ml basic fibroblast growth factor (bFGF, invitrogen 13256-029) to a basic culture solution comprising 20% Knockout Serum Replacement (available from Gibco Brl.) in Mema-gluta max (Gibco Brl., 32571) solution.

The culture solution collected from the culture of a MEF for 1 or 2 days may be used as a culture solution for culturing ICM. After centrifuging the collected culture solution using a centrifugal separator without filtering, a resulting supernatant (that is, conditioned medium) only may be used.

The culture solution for stem cells may also be prepared by the following method. First, an existing culture solution for stem cell lines, in which the embryonic stem cell line has already cultured, is recovered and centrifuged. A supernatant thereof is collected and mixed with a fresh culture solution in a mixing ratio by percentage of 50%:50% to prepare a conditioned medium used for establishment of a primary stem cell line. In this regard, using the conditioned medium may improve a success rate of culturing the stem cell from the blastocyst.

For cultivation of stem cell lines for medical treatment, the ICM may be optionally cultured in a culture dish without MEF or, alternatively, a mixture of Matrigel and PBS in a mixing ratio of 1:30 as well as 0.1% gelatin are stored on a surface of a culture dish at 4° C. for about 1 hour to coat the dish and the coated culture dish may be used for culturing the stem cell lines under the same conditions (for the cultivation using the culture dish without MEF described above), after discarding the content in the dish.

The culture solution may be replaced every 24 hours. Alternatively, if an mTsSR medium (available from Stem Cell Technologies) is replaced everyday instead of the culture solution, the embryonic stem cell lines may be cultured under an environment without the feeder cell. However, since the embryonic stem cell may differentiate into undesired cells, the ICM is generally cultured on the MEF.

When the embryonic stem cells are left to agglomerate and grow, a cell mass in an embryo form is formed and the embryonic stem cells begin self-differentiation. Cells derived from the ICM have potential for differentiation into three-germ layer cells. Accordingly, if the present invention is applied to development of novel and improved techniques for differentiation of embryonic stem cells into desired cells, these techniques may be effectively used for medical treatment of various diseases.

Hereinafter, the present invention will be described in greater detail by the following example. However, these examples are given for illustrative purposes and a person skilled in the art will appreciate that the present invention is not restricted thereto.

EXAMPLES

1. Preparation of Micro Cover Glass

As described above, in order to culture 30 to 40 cells called an inner cell mass while maintaining the inner cell mass un-differentiated, a micro cover glass was used.

In the present example, a micro cover glass with a size of 25 mm in width and 25 mm in length (manufactured by VWR International LLC, cat no. 48366-089) was processed by the following procedure and used.

Figure 4A:
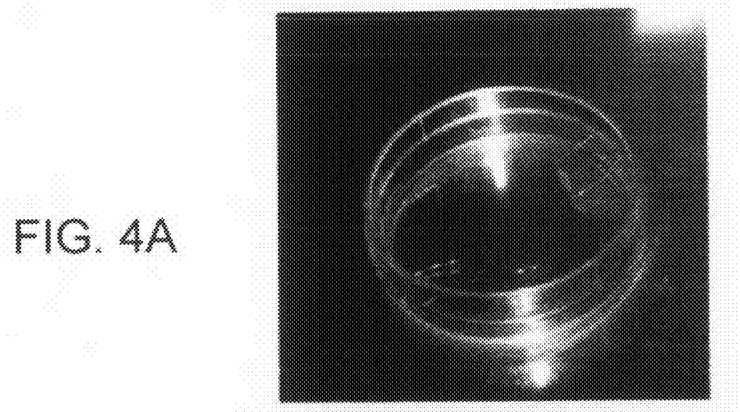
FIGS. 4A through 4C are photographs showing a process of forming a micro cover glass according to an exemplary embodiment of the present invention.
Figure 4B:
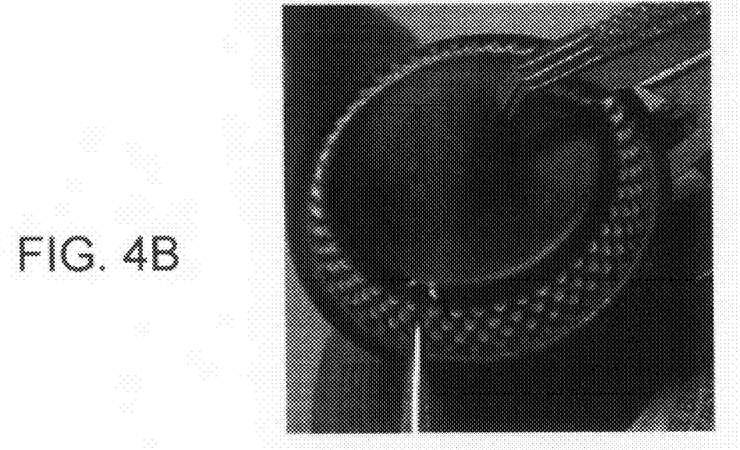
Figure 4C:
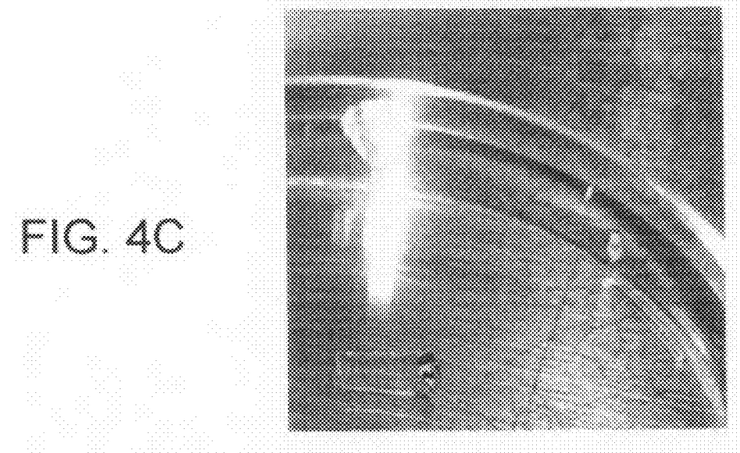

A typical micro cover glass with 25 mm (width)×25 mm (length) purchased in the market was cut into a small glass piece having a size of 7 mm (width)×5 mm (length) (FIG. 4A), followed by heating an end of the piece (FIG. 4B) so as to use the glass piece as a micro cover glass in the embodiment of the present invention. Due to a weight of the micro cover glass, the heated end was bent and deformed as shown in FIG. 4C. Next, using a 10 times diluted solution of hydrofluoric acid (48 to 51%), microfine scars found on a surface of a part of the micro cover glass (including a lifting part), which comes in contact with a blastocyst, were completely removed then cleaned.

2. Covering Blastocyst with Micro Cover Glass

Figure 5:
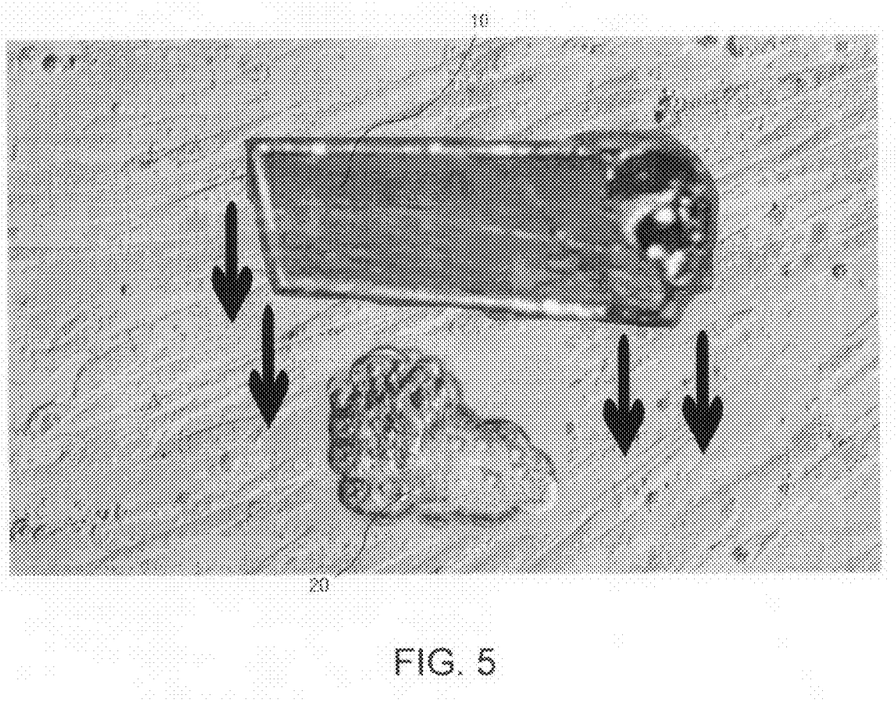
FIG. 5 is a photograph showing use of a micro cover glass to cover a blastocyst from which a zona pellucida has been removed.

The above processed micro cover glass was used to cover the blastocyst from which a zona pellucida had been removed, as shown in FIG. 5.

Figure 6:
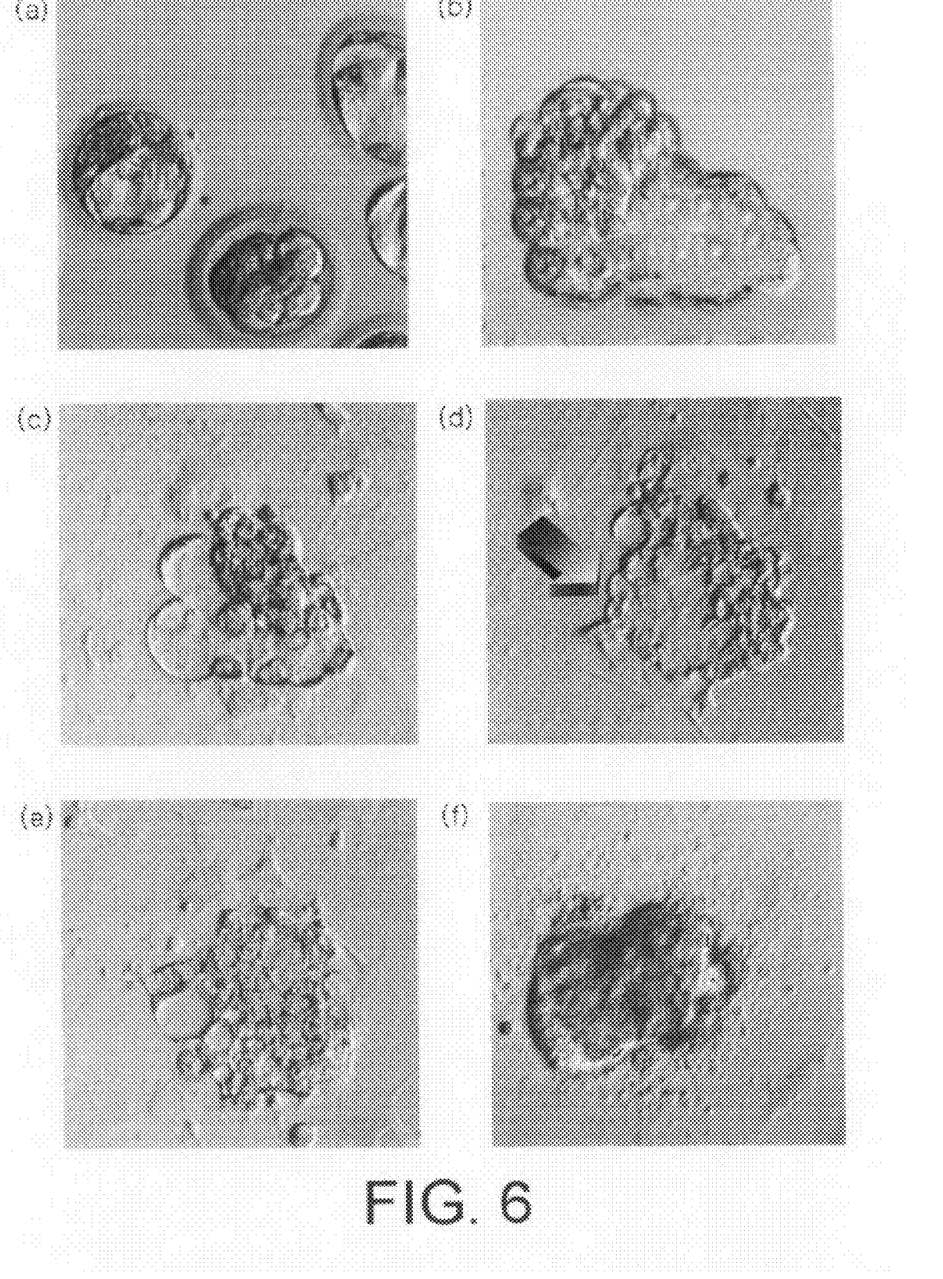
FIG. 6 is photographs showing the blastocyst before and after covering the same with the micro cover glass.

After in vitro culturing a fertilized ovum, the blastocyst after 5 to 6 days (FIG. 6(a)) was dissolved in 0.1% pronase for 1 to 2 minutes to remove the zona pellucida (FIG. 6(b)). The blastocyst without the zona pellucida was placed on a face of a feeder cell. A pair of forceps was used to grip the lifting part (that is, the bent end part) of the micro cover glass and gently cover the blastocyst with the micro cover glass. Hence, the blastocyst received a pressure caused by a weight of the micro cover glass. FIG. 6(c) is a photograph showing the blastocyst immediately after putting the micro cover glass on the blastocyst. 6 hours after pressing the blastocyst by the micro cover glass, stem cells in the ICM aggregate propagated toward a trophoblast layer and the trophoblast layer was gradually reduced (FIG. 6(d)). Moreover, 14 hours after pressing the blastocyst by the micro cover glass, the trophoblast layer was considerably reduced (FIG. 6(e)).

3. Preparation of Micro Cover Glass

After 14 hours when the blastocyst was covered by the micro cover glass, it was found that the trophoblast layer was almost removed while the stem cells proliferated from the ICM were positioned therein to replace the trophoblast layer. At this time, the micro cover glass was taken off. When removing the micro cover glass, the blastocyst fixed to the face of the feeder cell may sensitively respond to environment changes or external stimulus. According to the present inventive example, a micro-manipulator was used to take off the micro cover glass as shown in FIGS. 7A through 7D.

Figure 7A:
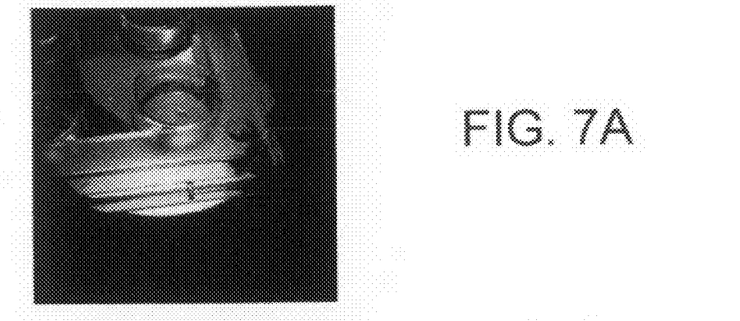
FIGS. 7A through 7D are photographs showing removal of the micro cover glass using a micro-manipulator.
Figure 7B:
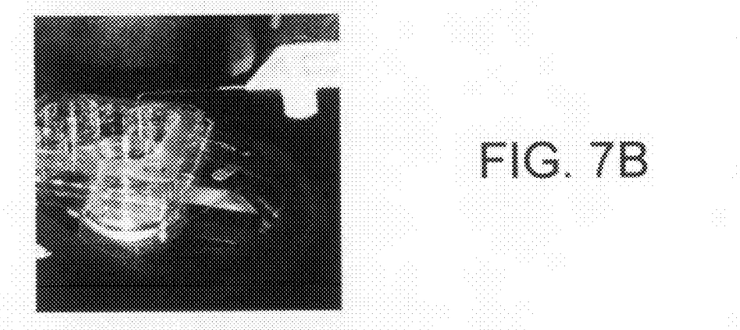
Figure 7C:
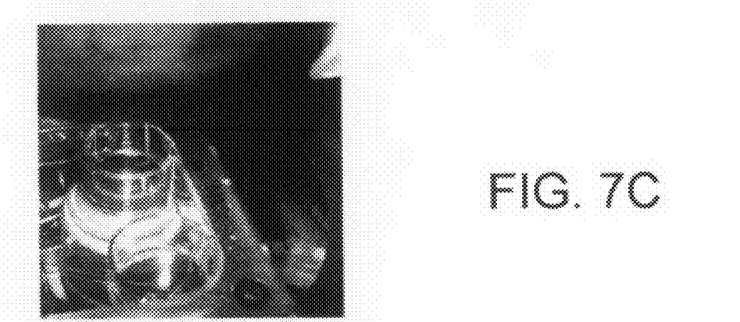
Figure 7D:
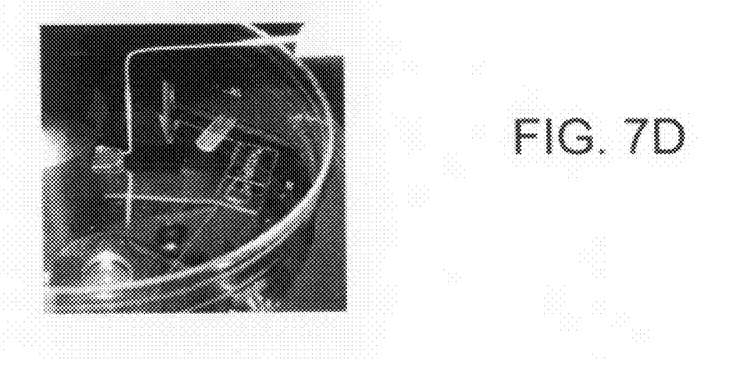

FIG. 7A is a photograph showing cultivation of the blastocyst covered using the micro cover glass, FIG. 7B is a photograph showing a micro-manipulator positioned upper portion of the culture dish, and FIG. 7C is a photograph showing the lifting part of the micro cover glass in the culture dish pressed using the micro-manipulator. FIG. 7D illustrates an operation principle in that, when the lifting part of the micro cover glass is pressed minutely and slowly using the micro-manipulator, the other part of the micro cover glass is lifted upward.

According to the inventive example, when the lifting part of the micro cover glass was pressed using the micro-manipulator to lift up the other part of the micro cover glass, the lifted part was moved to a position apart from the ICM using the micro-manipulator and the micro cover glass was taken off using the forceps.

4. Cultivation of Embryonic Stem Cell

Figure 8:
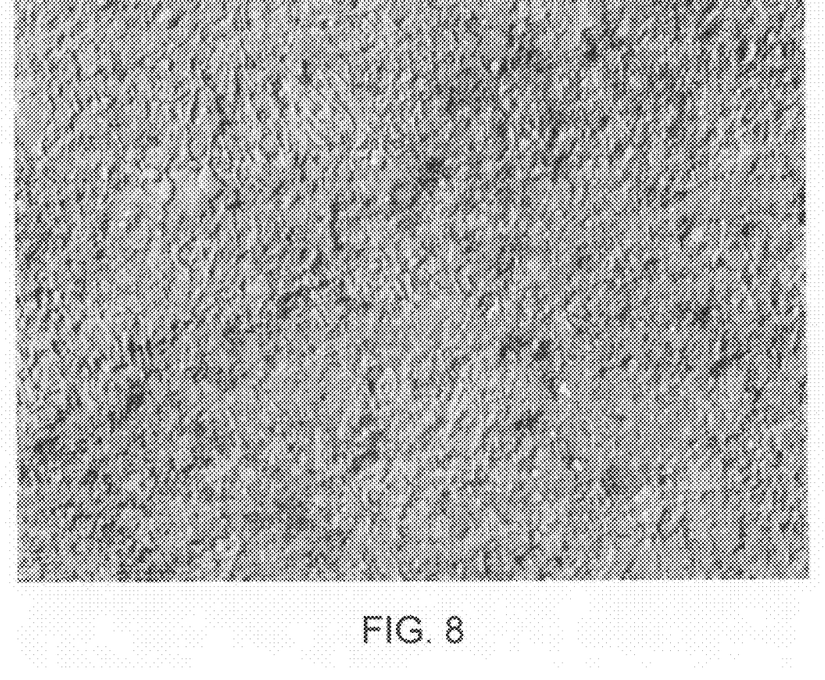
FIG. 8 is a photograph showing an embryonic stem cell line established according to an exemplary embodiment of the present invention.

After removing the micro cover glass, the isolated ICM (that is, stem cells) was cultured in a humidity saturation incubator with 5% carbon dioxide at 37° C. FIG. 6F is a photograph showing the cultured cells with lapse of time of about 2 to 3 days after culturing. An ICM was observed in the center part of FIG. 6F together with a plurality of un-differentiated embryonic stem cells in micro-particle scale growing around the center part. Repetitive subculture of the cultured embryonic stem cells resulted in establishment of an embryonic stem cell line as shown in FIG. 8. A method for subculturing the embryonic stem cells obtained in the present invention is substantially identical to any conventional method well known in the art.

The culture solution for the isolated ICM was replaced every 24 hours and the culture solution and the culture dish were prepared as follows.

5. Preparation of Culture Solution and Culture Dish for Culturing Embryonic Stem Cell Line (1) Preparation of Culture Solution for Embryonic Stem Cell Line A culture solution used in the present invention was produced by combining 20% Knockout Serum Replacement (available from Gibco Brl.) with Mema-gluta max (Gibco Brl., 32571) solution to prepare a basic culture solution, and adding 0.1 mM β-mercaptoethanol (Sigma), 100 units/ml penicillin, 100 μg/ml streptomycin and 4 ng/ml basic fibroblast growth factor (bFGF, invitrogen 13256-029) to the basic culture solution.

Before use, the prepared culture solution was co-cultured in MEF for 1 or 2 days, collected and centrifuged using a centrifugal separator. A resulting supernatant was mixed with a fresh culture solution in a mixing ratio by percentage of 50%:50% to prepare a conditioned medium for use.

(2) Preparation of Culture Dish

In a 4-well dish (Nunclon, cat no. 176740), a 10 times diluted solution of gelatin with 0.1% coating (Sigma G1393) was stored for 1 hour. This dish was used as the culture dish after discarding the content of the 4-well dish.

6. Preparation of MEF Feeder Cell Layer

Prior to transplantation of the ICM in the culture dish containing the MEF, 50 to 100 MEFs (that is, feeder cells), which have fixed to an area of 0.2 mm² in the culture dish to grow, were cultured in a culture solution containing 10 μg/ml of mitomycin C (Sigma) for 5 to 6 hours in order to decrease differentiation potential thereof. After washing the treated MEF with the culture solution for the embryonic stem cell, the culture dish was completed for culturing the MEF used as the feeder cell, on which the embryonic stem cells are grown.

COMPARATIVE EXAMPLE

An ICM was isolated from a blastocyst through immunosurgery. First, a zona pellucida of a fertilized ovum was dissolved in 0.1% pronase for 1 to 2 minutes, followed by storing a blastocyst mass present in the zona pellucida in a 100% anti-human serum antibody solution (Sigma) for about 20 minutes. Following this, the treated blastocyst mass was again stored in a guinea pig complement for about 30 minutes.

Figure 9:
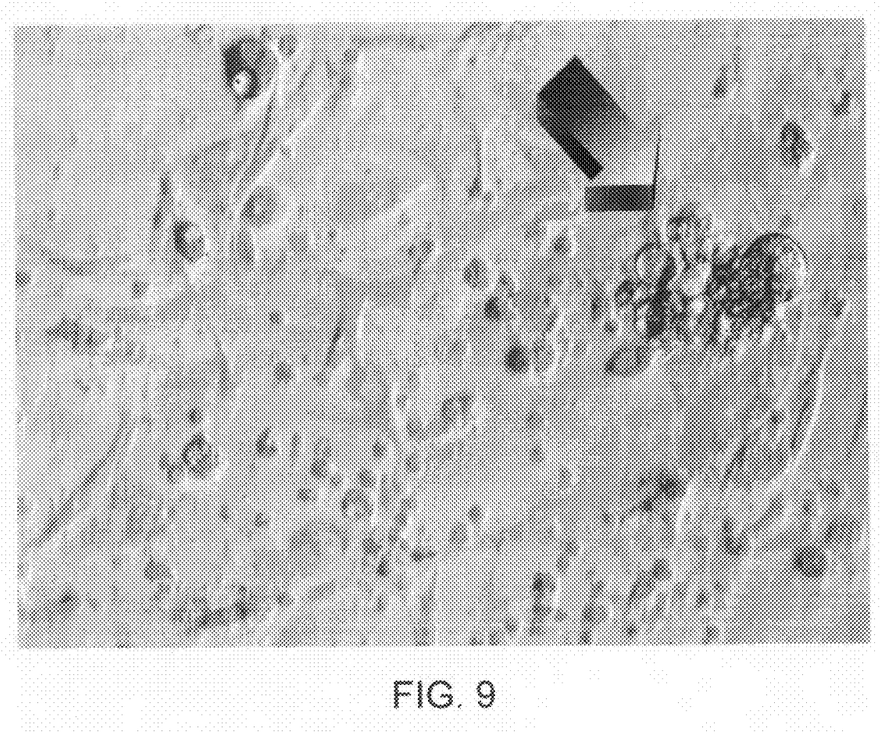
FIG. 9 is a photograph showing an inner cell mass isolated by a conventional immunosurgery.

The isolated cells were subjected to cultivation and proliferation according to the same process as described in the above example, so as to produce a final product, that is, an embryonic stem cell line (see FIG. 9).

Experimental Example 1

Comparison of Results for Establishment of Embryonic Stem Cell Lines Between Example and Comparative Example Establishment results of embryonic stem cell lines prepared according to the above Example and Comparative Example are shown in the following Table 1.

TABLE 1

| Section | Number of fertilized ovum blastocyst used in culturing | Number of inner cell mass fixed to face of feeder cell | Number of inner cell mass beginning to be cultured at face of feeder cell | Number of established embryonic stem cell line by culturing sufficient number of inner cell mass on feeder cell |
|---|---|---|---|---|
| Example | 5 | 5 (100%) | 5 (100%) | 4 (80%) |
| Comparative Example | 10 | 7 (70%) | 4 (40%) | 2 (20%) |

From the above Table 1, it can be seen that the method for isolation of an inner cell mass and a method for preparation of an embryonic stem cell line according to an embodiment of the present invention exhibit remarkably improved success rates, compared to those disclosed in the art, more particularly, the conventional immunosurgery and the conventional method for preparation of an embryonic stem cell line using an inner cell mass isolated by the conventional immunosurgery. Consequently, the inventive cultivation method may produce a large amount of embryonic stem cell lines with potential for differentiation into various cell types, thereby being effectively applied in medical applications and/or studies using embryonic stem cells.

Experimental Example 2

Comparison of Results According to the Spacer Sizes

Glass fiber having an average diameter of 10 μm to 15 μm was used. The diameter of the blastocyst cell mass was 100 μm to 130 μm.

When the blastocyst was covered by the micro cover glass without a spacer, a space of 2 to 3 μm was formed due to the feeder cell.

In order to make spacers each making a space of 10 μm-15 μm and 20 μm-30 μm, plural glass fibers were stacked on the feeder cells.

In order to make a spacer of 50 μm-100 μm, the cover glass were bent at the four corners and used.

The blastocyst was covered by the micro cover glass with each spacer for 13 hours. The other culture conditions are the same as the above Example and Comparative Example.

Table 2 shows the results according to the sizes of the spacers between the feeder cell and the cover glass.

TABLE 2

| | Number of fertilized ovum blastocyst used in culturing | Number of inner cell mass fixed to face of feeder cell | Number of inner cell mass beginning to be cultured at face of feeder cell | Number of established embryonic stem cell line by culturing sufficient number of inner cell mass on feeder cell |
|---|---|---|---|---|
| Natural spacer 2 μm-3 μm | 28 | 28 (100%) | 13 (46.4%) | 10 (35.7%) |
| Spacer 10 μm-15 μm | 26 | 26 (100%) | 16 (61%) | 13 (50%) |
| Spacer 20 μm-30 μm | 28 | 28 (100%) | 24 (85.7%) | 22 (78.5%) |
| Spacer 50 μm-60 μm | 24 | 15 (62.5%) | 10 (41.6%) | 8 (33%) |
| Spacer 70 μm-80 μm | 12 | 4 (33.3%) | 2 (16.6%) | 2 (16.6) |
| Spacer 90 μm-100 μm | 16 | 2 (12.5%) | 1 (6.2%) | 1 (6.2%) |

As shown in Table 2, when the spacer made a space of 20 μm-30 μm, the percentage of the inner cell mass fixed to the face of the feeder cell was 100%, and the percentage of the established embryonic stem cell lines was 78.5%. When there is no spacer between the cover and the feeder cell, the percentage of the established embryonic stem cell lines was 35.7%. When the space made from the spacer is over 50 μm, the number of the inner cell mass fixed to the face of the feeder cell was low compared with the results from the spacers of 10 μm-15 μm and 20 μm-30 μm, and the percentage of the established embryonic stem cell lines was 33%. In view of the above results, the spacer making a space of 4 μm to 40 μm is preferred, the spacer making a space of 10 μm to 30 μm is more preferred, and the spacer making a space of 20 μm to 30 μm is much more preferred.

While the present invention has been described with reference to preferred embodiments, it will be understood by those skilled in the art that various modifications and variations may be made therein without departing from the scope of the present invention as defined by the appended claims.

What is claimed is:

1. A method for isolation of an inner cell mass, comprising:
   placing a morula or a blastocyst being free from a zona pellucida on a feeder cell or a feeder-independent medium;
   putting a micro cover glass on the morula or the blastocyst to cover and apply pressure to the morula or the blastocyst for a desired time to destroy a trophoblast layer and isolate the inner cell mass from the morula or the blastocyst; and
   removing the micro cover glass from the isolated inner cell mass;
   wherein a spacer is present on at least one of the micro cover glass and the feeder cell or between the micro cover glass and the feeder cell to make a space between the micro cover glass and the feeder cell.

2. The method according to claim 1, wherein the micro cover glass has a lifting part.

3. The method according to claim 2, wherein the lifting part is a ring mounted on the micro cover glass or a bent end of the micro cover glass.

4. The method according to claim 1, wherein the pressure caused by the weight of the micro cover glass ranges from 0.001 to 0.003 g/mm$^2$.

5. The method according to claim 1, wherein a period of time to cover the morula or the blastocyst with the micro cover glass ranges from 3 to 20 hours.

6. The method according to claim 1, wherein the micro cover glass has a size of 3 to 8 mm in width and 2 to 6 mm in length.

7. The method according to claim 1, wherein a tool selected from pincettes, forceps or a micro-manipulator is used to cover the morula or the blastocyst with the micro cover glass or to remove the micro cover glass from the morula or the blastocyst after the desired time.

8. The method according to claim 1, wherein the step of placing the morula or the blastocyst comprises placing the blastocyst being free from the zona pellucida on the feeder cell.

9. The method according to claim 1, wherein the blastocyst being free from the zona pellucida is treated using trichostatin-A beforehand.

10. A method for preparation of an embryonic stem cell line, comprising:
    placing a morula or a blastocyst being free from a zona pellucida on a feeder cell or a feeder-independent medium;
    putting a micro cover glass on the blastocyst to cover and apply pressure to the morula or the blastocyst for a time sufficient to destroy a trophoblast layer and isolate an inner cell mass from the morula or the blastocyst; and
    proliferating the isolated inner cell mass;
    wherein a spacer is present on at least one of the micro cover glass and the feeder cell or between the micro cover glass and the feeder cell to make a space between the micro cover glass and the feeder cell.

11. The method according to claim 10, further comprising removing the micro cover glass from the isolated inner cell mass.

12. A method for isolation of an inner cell mass, comprising:
    placing a blastocyst being free from a zona pellucida on a feeder cell; and
    putting a cover on the blastocyst with a space ranging from 4 micrometer to 40 micrometer between the cover and the feeder cell to destroy a trophoblast layer and isolate the inner cell mass from the blastocyst;
    wherein a spacer is present on at least one of the cover and the feeder cell or between the cover and the feeder cell to make the space between the cover and the feeder cell.

13. The method of claim 12, wherein the spacer is legs mounted on the cover, and the legs have a length of 4 micrometer to 40 micrometer to make the space between the cover and the feeder cell when the cover is put on the blastocyst.

14. The method of claim 12, wherein the spacer is a glass fiber put on the blastocyst.

15. The method of claim 12, wherein the spacer is a nylon filament or a plastic filament.

16. The method of claim 12, wherein the space ranges from 10 micrometer to 30 micrometer.

17. The method of claim 12, wherein the space ranges from 20 micrometer to 30 micrometer.

18. A method for preparation of an embryonic stem cell line, comprising proliferating the inner cell mass isolated by the method as set forth in claim 12.

\* \* \* \* \*